United States Patent
Kim et al.

(10) Patent No.: US 9,332,962 B2
(45) Date of Patent: May 10, 2016

(54) ULTRASOUND ARFI DISPLACEMENT IMAGING USING AN ADAPTIVE TIME INSTANCE

(71) Applicants: Seungsoo Kim, Kirkland, WA (US); Liexiang Fan, Sammamish, WA (US); Nikolas M. Ivancevich, Seattle, WA (US); David P. Duncan, Renton, WA (US)

(72) Inventors: Seungsoo Kim, Kirkland, WA (US); Liexiang Fan, Sammamish, WA (US); Nikolas M. Ivancevich, Seattle, WA (US); David P. Duncan, Renton, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 285 days.

(21) Appl. No.: 13/801,400

(22) Filed: Mar. 13, 2013

(65) Prior Publication Data

US 2014/0276046 A1    Sep. 18, 2014

(51) Int. Cl.
  *A61B 8/08*  (2006.01)
  *A61B 8/14*  (2006.01)
  *G01S 7/52*  (2006.01)
  *G01S 15/89* (2006.01)

(52) U.S. Cl.
  CPC . *A61B 8/485* (2013.01); *A61B 8/08* (2013.01); *A61B 8/5223* (2013.01); *A61B 8/5269* (2013.01); *G01S 7/52042* (2013.01); *G01S 7/52071* (2013.01); *G01S 15/8915* (2013.01); *A61B 8/488* (2013.01); *G01S 15/8979* (2013.01)

(58) Field of Classification Search
  CPC .......... A61B 8/08; A61B 8/485; A61B 8/488; A61B 8/5223; A61B 8/5269; G01S 7/52042; G01S 7/52071; G01S 15/8915; G01S 15/8979
  See application file for complete search history.

(56) References Cited

U.S. PATENT DOCUMENTS

| | | | | |
|---|---|---|---|---|
| 7,374,538 | B2 * | 5/2008 | Nightingale et al. | 600/443 |
| 8,043,216 | B2 * | 10/2011 | Matsumura | 600/438 |
| 8,118,744 | B2 * | 2/2012 | Palmeri et al. | 600/437 |
| 8,469,891 | B2 * | 6/2013 | Maleke et al. | 600/438 |
| 2004/0167403 | A1 * | 8/2004 | Nightingale et al. | 600/437 |
| 2008/0249408 | A1 * | 10/2008 | Palmeri et al. | 600/438 |
| 2008/0269606 | A1 * | 10/2008 | Matsumura | 600/438 |
| 2010/0317971 | A1 | 12/2010 | Fan et al. | |
| 2012/0089019 | A1 | 4/2012 | Fan | |
| 2012/0108968 | A1 | 5/2012 | Freiburger et al. | |
| 2012/0215101 | A1 | 8/2012 | Maleke et al. | |
| 2013/0066204 | A1 * | 3/2013 | Fan et al. | 600/438 |
| 2013/0218011 | A1 * | 8/2013 | Benson et al. | 600/438 |
| 2013/0345565 | A1 * | 12/2013 | Fan et al. | 600/442 |

OTHER PUBLICATIONS

Dahl et al., "A Parallel Tracking Method for Acoustic Radiation Force Impulse Imaging", IEEE Transactions on Ultrasonics, Ferroelectrics, and Frequency Control, vol. 54, No. 2, Feb. 2009.*

* cited by examiner

*Primary Examiner* — Long V Le
*Assistant Examiner* — Colin T Sakamoto

(57) ABSTRACT

In ARFI imaging, a cost function is used to identify a time of displacement that best or sufficiently indicates the desired information. For example, the displacements associated with a combination of contrast and signal-to-noise ratio are identified. The time at which the desired displacements occur may be other than the time of the maximum. Since the time is common to displacements for one or more scan lines, the displacement image may be assembled line-by-line or by groups of lines.

19 Claims, 3 Drawing Sheets

ULTRASOUND ARFI DISPLACEMENT IMAGING USING AN ADAPTIVE TIME INSTANCE

BACKGROUND

The present embodiments relate to ultrasound imaging. In particular, acoustic radiation force impulse (ARFI) imaging may be improved.

In ARFI imaging, a shear, longitudinal or other wave is generated with an ARFI transmitted as a push pulse. Ultrasound energy is transmitted to a focal region to generate the wave, resulting in displacement of tissue around the focal region. Further ultrasound scanning tracks the displacement of tissue over time at locations around the focal region. For each location, the peak or maximum displacement is determined and used to generate an image. However, maximum displacement may be biased because parts of tissues may accumulate more displacements than other parts during the transient response of the ARFI.

The wave information may indicate tissue characteristics in addition to acoustic impedance (e.g., B-mode) and Doppler (e.g., flow mode) imaging. ARFI imaging may provide tissue elastic properties based on tissue displacements induced by ARFIs. Wave velocity information may be useful for diagnosis. The wave velocity is determined as the time to reach the maximum displacement. However, the bias in the maximum displacement may cause errors in the derived information.

BRIEF SUMMARY

By way of introduction, the preferred embodiments described below include methods, instructions, and systems for ARFI imaging. A cost function is used to identify a time of displacement that best or sufficiently indicates the desired information. For example, the displacements associated with a combination of contrast and signal-to-noise ratio are identified. The time at which the desired displacements occur may be other than the time of the maximum. Since the time is common to displacements for one or more scan lines, the displacement image may be assembled line-by-line or by groups of lines.

In a first aspect, a method is provided for ARFI imaging. An ultrasound system measures displacements over different times at a plurality of locations within a patient in response to an impulse excitation. Contrasts are determined for the displacements at each of the times. Signal-to-noise ratios are determined for the displacements at each of the times. A first (not necessarily the earliest time) one of the times is selected as a function of the contrasts and the signal-to-noise ratios. An ARFI image is generated with the displacements of the selected first time.

In a second aspect, a non-transitory computer readable storage medium has stored therein data representing instructions executable by a programmed processor for ARFI imaging. The storage medium includes instructions for determining displacements at multiple times, calculating quality levels of the displacements for the times with a cost function, identifying one of the times based on the quality levels, and outputting an image with display values modulated by the displacements of the one time.

In a third aspect, a system is provided for ARFI imaging. A transducer is configured to transmit a first acoustic impulse excitation into a patient, configured to scan with ultrasound a first line of the patient, configured to transmit a second acoustic impulse excitation into the patient, and configured to scan with ultrasound a second line of the patient. A receive beamformer is configured to generate data representing the first and second lines at different times relative to the first and second acoustic impulse excitations, respectively. The data is generated from the scans with ultrasound. A processor is configured to estimate tissue displacement in the first and second lines induced by the first and second acoustic impulse excitations at each of the different times and configured to select a first of the different times for the tissue displacements in the first line and to select a second of the different times for the tissue displacements in the second line. The first time is a different amount of time after the first acoustic impulse excitation than the second time after the second acoustic impulse excitation. A display is configured to display an image representing the displacements of the first time for the first line and of the second time for the second line.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

ARFI displacements at a certain time instance are displayed since such displacements may more heavily rely on only tissue elasticity than using maximum displacement. Tissue elasticity is the desired characteristic for an ARFI image. The displacements at a certain time rely on the ARFI (push beam) intensity in the field, which may be modeled and compensated for with the model.

The ARFI displacement image is adaptively displayed by analyzing a cost function. In order to pick-up the correct time instance of the ARFI displacement sequence, the cost function evaluates the ARFI displacements. Based on the definition of the cost function, the ARFI displacement image may be optimized for different patients, types of examinations, different user desired results, and/or different tissue types.

Figure 1:
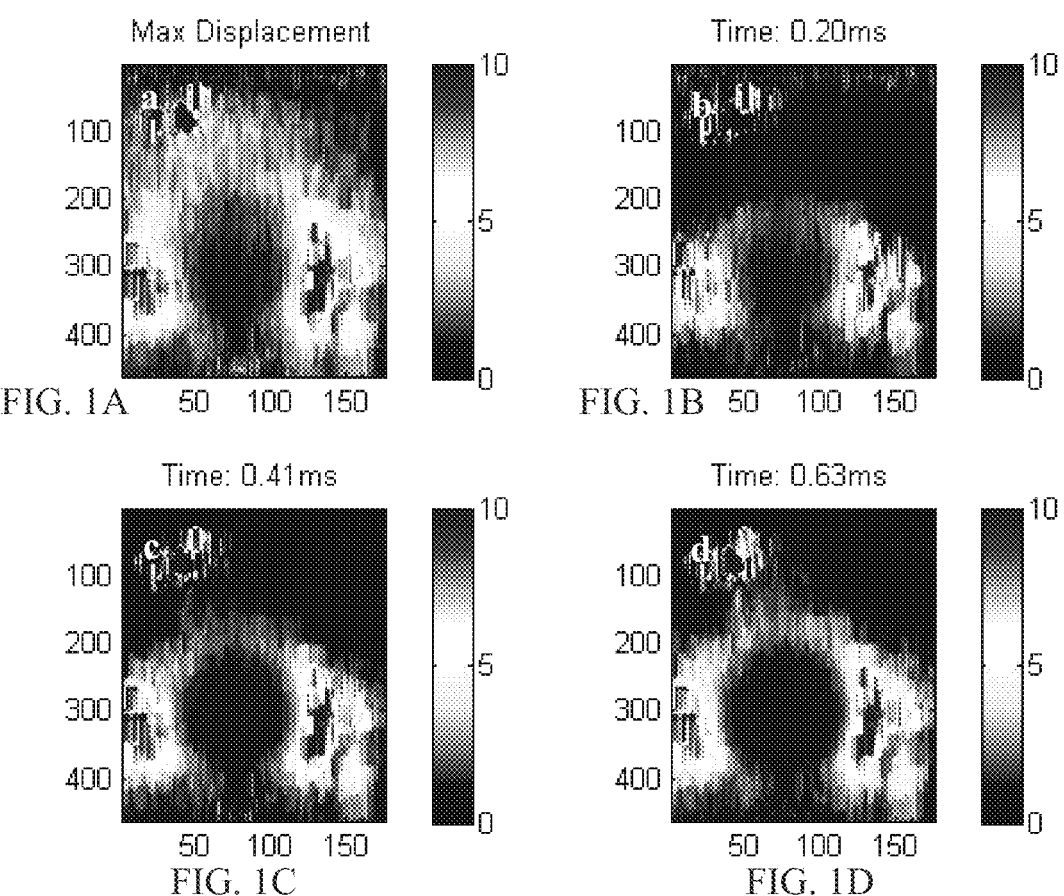
FIG. 1A is an example acoustic radiation force impulse (ARFI) image using maximum displacement.
FIGS. 1B-D are example acoustic radiation force images of displacements at particular times.

FIGS. 1A-D show examples of ARFI displacement images. FIG. 1A shows a maximum displacement where the maximum displacement at each pixel is accumulated over time. As another displacement is measured for a given location, the displacement is compared to the accumulated displacement. The maximum is stored. The maximum displacement image provides some tissue elasticity information. However, the near field tissue being soft (e.g., more displacement) may be the result of tissue displacement accumulation over time, which does not necessarily mean softer tissue than other parts.

FIGS. 1B-D show the displacements at certain times. Each planar image represents displacements at or near a same time after one or more pushing pulses. Different parts of the images may be responsive to different pushing pulses due to the ARFI scan pattern, but the represented displacements have the same or similar timing relative to the respective ARFI. Similar accounts for timing tolerances and/or single cycle phase differences. FIG. 1B shows displacements at 0.20 ms, FIG. 1O shows displacements at 0.41 ms, and FIG. 1D shows displacements at 0.63 ms. Other timing examples are possible. The displacements at FIGS. 1B-D are different than the accumulated maximum displacements of FIG. 1A, and may have better border definition, contrast resolution, signal-to-noise ratio or other characteristics than the maximum displacement image.

By establishing the cost function based on the desired factors in ARFI displacement images, back-end optimization of ARFI displacement image is possible. By analyzing the cost function at each time instance, the time instance providing the desired factor or factors is identified. The ARFI displacement image may not be based on maximum displacement and may not be based on a time to peak displacement (e.g., not a wave velocity image).

Figure 2:
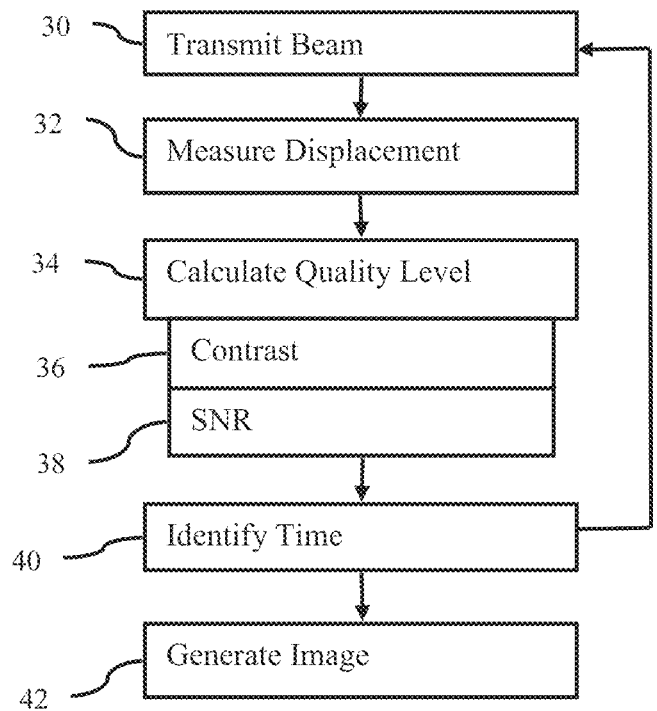
FIG. 2 is a flow chart diagram of one embodiment of a method for ARFI imaging with temporal selection.

FIG. 2 shows a method for ARFI displacement imaging. The method is implemented by the system of FIG. 4 or a different system. Additional, different, or fewer acts may be provided. For example, act 30 is not performed and the source of stress is provided by the body, manually, using a thumper, or by other mechanism. As another example, different cost factors are calculated instead of SNR in act 38 and/or contrast in act 36. The acts are performed in the order described or shown, but may be performed in other orders.

The description of the method of FIG. 2 is provided in the context of an example represented in FIGS. 1A-D. FIGS. 1A-D show ARFI displacement images of a two dimensional region of a phantom. The method can be used for human tissue. The region has a hard inclusion (darker circular region). More than one lesion or tumor may be in a region of human or other tissue. The method is performed for each of the B-mode or scan sample locations in an entire field of view or a region of interest. Less or more dense sampling may be used.

In act 30 of FIG. 2, an acoustic excitation is transmitted into a patient. The acoustic excitation acts as an impulse excitation, so is an ARFI. For example, a 400 cycle transmit waveform with power or peak amplitude levels similar or higher than B-mode transmissions for imaging tissue is transmitted. In one embodiment, the transmission is one of multiple pushing pulses applied as a radiation force sequence to the field of view. Any acoustic radiation force impulse (ARFI) sequence may be used.

The transmission is configured by power, amplitude, timing or other characteristic to cause stress on tissue sufficient to displace the tissue at one or more locations. For example, a transmit focus is positioned near a bottom, center of the field of view to cause displacement throughout the field of view. The transmission may be repeated for different sub-regions.

The excitation is transmitted from an ultrasound transducer. The excitation is acoustic energy. The acoustic energy is focused, resulting in a three-dimensional beam profile. The excitation is focused using an array of elements and/or mechanical focus. The excitation may be unfocused in one dimension, such as the elevation dimension. The excitation is transmitted into tissue of a patient.

In act 32, displacements of the tissue in the patient are measured. The excitation causes displacement of the tissue. A shear, longitudinal, or other wave is generated and propagates from the focal region. As the wave travels through tissue, the tissue is displaced. The tissue is forced to move in the patient.

The displacement caused by the force or stress is measured. The displacement is measured over time at one or more locations. The displacement measurement may begin before the stress or impulse ends, such as using a different frequency or coding. Alternatively, the displacement measurement begins after the impulse ends. Since the shear, longitudinal or other wave causing the displacement in tissue spaced from the point or region of stress takes time to travel, the displacement from a relaxed or partially stressed state to a maximum displacement and then to a relaxed state may be measured. Alternatively, the displacement is measured only while the tissue is relaxing from the maximum.

The measurement is of the amount or magnitude of the displacement. The tissue is moved in any direction. The measurement may be along the direction of greatest movement. The magnitude of the motion vector is determined. Alternatively, the measurement is along a given direction, such as perpendicular to or along the scan line regardless of whether the tissue is displaced more or less in other directions.

The displacement is detected with ultrasound scanning. A region, such as a region of interest, entire field of view, or sub-region of interest, is scanned with ultrasound. Any now known or later developed displacement imaging may be used. For example, pulses with 1-5 cycle durations are used with an intensity of less than 720 mW/cm$^2$. Pulses with other intensities may be used.

For a given sample time, ultrasound is transmitted to the tissue or region of interest. Echoes or reflections from the transmission are received. The echoes are beamformed, and the beamformed data represents one or more locations. Any transmission and reception sequence may be used.

By performing the transmitting and receiving multiple times, data representing a one, two, or three-dimensional region at different times is received. The transmission and reception are repeated to determine change due to displacement. By repetitively scanning with ultrasound, the position of tissue at different times is determined.

Figure 3:
FIG. 3 is an example illustration of the displacements over depth for different line scanning times.

FIG. 3 shows measuring displacement along a scan line at three different scan times. Each line represents distance or depth along the scan line at a different scan time $t_2$ (e.g., sequential scan of the line). For sampling along the line once (e.g., one scan time $t_2$), the samples from different times $t_1$ are acquired. The scan of the line is repeated at other times $t_2$ to acquire sets of samples for different depths at different scan times. Any number of samples per line may be acquired. Any number of repetitions of scanning the line may be performed. Any number of lines may be scanned at a given time.

The echoes are detected using B-mode or Doppler detection. The displacement is detected from the differences for each spatial location. For example, the velocity, variance, shift in intensity pattern (e.g., speckle tracking), or other information is detected from the received data as the displacement.

In one embodiment using B-mode data, the data from different scans is correlated. For example, a current set of data is correlated multiple times with a reference set of data. The location of a sub-set of data centered at a given location in the reference set is identified in the current set. For each location, a windowed set of data is correlated with the reference data. The window is centered on the location. Different relative translations and/or rotations between the two data sets are performed. In another embodiment, the correlation is performed along the axial direction only to determine displacement in this one direction.

The reference is a first set of data or data from another scan. The same reference is used for the entire displacement detection or the reference data changes in an ongoing or moving window.

The correlation is one, two or three-dimensional. For example, correlation along a scan line away and toward the transducer is used. For a two dimensional scan, the translation is along two axes with or without rotation. For three dimensional scanning, the translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

By repeating the scanning and displacement detection, displacements associated with different scan times are acquired. For a given location, a magnitude of displacement between scans is determined. By repeating scans, the displacement as a function of time for each of the locations is detected.

Other processes may be performed on the displacements. For example, the displacements are temporally and/or spatially filtered, such as with a low pass filter. As another example, the displacements are compensated for attenuation. Depth gain compensation is performed. The displacement as a function of depth may be modeled or empirically determined. Different intensity of ARFI pushing pulses may result in different depth attenuation profiles. The displacements as a function of depth may be compensated to account for the attenuation appropriate for a given intensity of pushing pulse.

As shown in FIG. 3, the results are displacements as a function of location and time. For example, displacements for multiple locations of a scan line are acquired for different scan times after the ARFI. Any temporal sampling period or repetition rate may be used. As another example, displacements for multiple locations in a two or three-dimensional region are acquired for the different times. The displacements may be from scanning multiple scan lines at a same time or from combining displacements based on timing relative to different ARFI into sets representing the locations at the same or similar time relative to the respective ARFI.

In act 34, the quality level of the displacements is calculated. The quality level is a measure or value of quality of the displacements, not the ultrasound signals (e.g., beamformed and/or detected signals). Quality of other information than displacements may used instead or in addition to quality of the displacements.

ARFI imaging may provide tissue elastic properties based on tissue displacements induced by ARFIs. There are several different ways to display the final ARFI displacement image, such as a display of ARFI induced maximum displacements at each pixel or a display of ARFI induced displacements at a certain time point. In the case of maximum displacement, the ARFI image may misrepresent the tissue elasticity due to the accumulation of surrounding tissue displacements. In the case of displacements at a certain time, determination of the proper time point is desired because an ARFI image may look different at each time point, resulting in false diagnostic outputs.

By establishing quality as a function of time, the desired time may be determined. The displacements of one time may be compared to the displacements of another time. For example, the displacements along a scan line acquired in one scan are compared to displacements acquired in another scan. While the displacements in a given scan for different locations are associated with different times $t_1$ within the scan, the times $t_2$ of the different scans are used to measure quality. The times between repetitions of the scanning the same locations is used. Alternatively, the time within a scan is used. The displacements with the desired elasticity representation or information are identified by the time of the scan relative to the ARFI. The displacements may describe image quality at each time instance to find the optimal time point.

Quality is used as a relative term. The quality is of displacements of one time relative to displacements of another time. The quality may be specific to the patient, application, physician, organ, and/or other consideration to assist in diagnosis in a particular situation. The measure of quality may be different depending on the people, tissue, and/or condition involved. The quality is indicative of one or more of various considerations. The signal-to-noise ratio, contrast, variance, contrast-to-noise ratio, border definition, gradients change, and/or other considerations may indicate the quality. Acts 36 and 38 represent use of the SNR and contrast considerations, but additional, different, or fewer parameters may be calculated to determine quality level of the displacements for a given scan time. For example, quality level may be measured as SNR, contrast-to-noise ratio, entropy, texture, and/or other statistical moments.

The level of quality is calculated with a cost function. The cost function uses parameters derived from the displacements rather than the displacements themselves (i.e., not accumulation of the maximum). Any cost function using any measure of the considerations may be used. For example, a cost function based on contrast and the signal-to-noise ratio of the displacements is used. This cost function may be represented as cost, $g(t)$=displacement $C(t)$* displacement $SNR(t)$ where displacement $C(t)$ is the contrast of the displacement, and displacement $SNR(t)$ is the signal-to-noise ratio of the displacement. In another example, contrast-to-noise ratio is used instead of or in addition to the contrast. The contrast measure may be divided by a noise measure, providing the contrast-to-noise ratio.

Multiplication is used for the cost function. Other relationships may be used, such as ratio, division, addition, subtraction, or other functions. Weighting and/or scaling may be applied, such a weighting the contribution from contrast more strongly than from SNR. Any of various combinations of information for the cost function may be used.

In act 36, contrast is determined for the displacements. Contrast is a spatial measure, so the contrast associated with displacements for a region is calculated. For example, the contrasts for displacements along a scan line are measured. Alternatively, a moving window is used to determine contrast associated with groups or each sample along the line or in another region.

In one embodiment, the contrast is represented by subtracting a minimum displacement from a maximum displacement for a given scan time. In the scan line example, the minimum displacement for a given frame (e.g., a given time corresponding to one of two frames of data used to determine the displacement) is subtracted from the maximum displacement for the same given frame. This contrast function generalized to a two-dimensional region is represented as displacement $C(t)=(\max(\text{displacement}(x,y,t))-\min(\text{displacement}(x,y,t))$ where displacement(x,y,t) is displacement by location x, y at the time instance t. Other contrast functions may be used. Contrast-to-noise is determined by dividing the contrast by a noise value. The contrast values may be spatially and/or temporally filtered.

In act 38, the signal-to-noise ratio (SNR) for the displacements is determined. The SNR may be determined for each displacement or by groups of displacements. One or more SNR values are determined for the displacements of a given scan time. Where multiple SNR values are provided for a given time, the SNR may be averaged or otherwise combined. For different scan times, different SNR values are calculated.

Any SNR function may be used. For example, the displacements are spatially filtered. In the scan line embodiment, the displacements along the scan line for a same scan time are low pass filtered. Any amount of filtering, cut-off frequency, and/or other characteristic may be used. Infinite impulse response or finite impulse response filtering may be used. Any number of displacements may be used, such as providing a moving window of two or more input locations.

To calculate SNR, the filtered displacement for a given location is subtracted from the unfiltered displacement for that location at the same time. The output of the filter is subtracted from the input of the filter. By dividing the unfiltered displacement for the location and time by the results of the subtraction, a SNR value is provided. This SNR function, generalized to two-dimensions and determining for different scan times, may be represented as Displacement SNR(t)=displacement(x,y,t)/(displacement(x,y,t)−filtered displacement (x,y,t)). The SNR values may be spatially and/or temporally filtered.

Other measures of SNR for displacement at a location and a time may be used. In another embodiment, the SNR is calculated using a quantification of the noise. The root mean square (RMS) of the noise signal is calculated to represent the noise level. Other calculations may be used, such as an average of the absolute values of the peaks in a profile of displacement by location. The signal level is calculated as the area under the filtered displacement profile. The integral of a filtered displacement is calculated. Other signal level measurements may be used. The SNR is provided by dividing the signal (e.g., integral of the filtered displacement) by the noise (e.g., RMS of the noise). Other functions may be used, including other variables.

In act 40, the quality levels are used to identify a time instance and corresponding displacement or displacements. Quality levels are determined for regions (e.g., single location, line, area, or volume) over different scan times. The displacements with the more desirable quality level (e.g., highest) are identified. Since the quality level is determined for the same locations at different times, identifying the time indicates the displacements.

The relative results of the cost function indicate the scan time of the displacements with the least cost. For example, the displacements associated with one time have a higher quality than displacements for another time. Depending on the structure of the cost function, a higher or lower cost maps to a more desirable quality (e.g., higher value may indicate a lesser quality).

In the contrast multiplied by SNR example, the time associated with a higher result is identified as having a higher quality. The higher result indicates higher contrast and/or higher SNR, both of which are desired. By weighting the contrast relative to SNR, the combination may skew towards a quality considered more important in a given imaging situation.

Given the input variables of contrast and SNR or a cost with other variables, the time with the highest quality level is selected. There may be any number of times, such as ten, twenty, fifty, seventy-five or more. The scan time after the ARFI with the best or maximum quality is selected from the pool of scan times. The optimal time instance, T, is determined. Time is used as an index or indication of the frame or set of displacements corresponding to the highest quality. In alternative embodiments, the displacements are indexed by another value than time. The displacements with the highest quality are selected.

As represented by the feedback from act 40 to act 30, the measuring, determining quality (e.g., determining contrasts and determining signal-to-noise ratios), and selecting are repeated for other regions. In a scan line-by-scan line approach, the repetition is for another scan line or group of scan lines. The displacements and corresponding quality levels for different scan or tracking times relative to the respective ARFI are determined. The time and corresponding displacements associated with the highest quality for the current scan line or scan lines are selected. In other embodiments, each repetition is for different regions (e.g., sub-areas or sub-volumes) other than by scan lines.

The repetitions are for different spatial locations in a region of interest. Using repetition may result some locations associated with one time relative to the ARFI and other locations associated with a different time relative to the respective ARFI. The same time may result for two, more, or all repetitions. Since the same time is likely to have similar cost, the selected times of the repetitions are likely to have similar (e.g., within 10%) times.

In another embodiment, a single time is selected based on multiple passes. The different times relative to respective ARFIs are combined, such as averaged. A first pass may provide a time of 0.33 ms after a first ARFI for one line, and a second pass may provide a time of 0.37 ms after a second ARFI for an adjacent line. The two times are averaged or one is selected (e.g., select the median). The displacements from the selected time are used for each line, such as using displacements at 0.35 ms.

Alternatively, no repetition is performed. Where a single transmission and reception scan format allows for scanning the entire region of interest, no repetition is needed and a single identification of time indicates the displacement data for the entire region of interest. The resulting displacements correspond to a same time. A single time is selected from one pass through of the method.

The displacements are selected for any size region. In one embodiment, the displacement is detected in a region of interest likely to include the tissue to be diagnosed, such as about ⅓ to ½ the complete scan region for B-mode imaging. Greater, lesser, or no region of interest may be used, such as detecting displacement over the entire imaging region. Narrower regions of interest may allow for displacement detection with fewer repetitions of transmitting ARFIs. Depending on the number of receive beams that may be formed and the sample density, none, one, or more repetitions may be used.

In act 42, an ARFI image is generated. The ARFI image is generated with the displacements from the selected time. Where different times are selected for different locations, the image is generated with the displacements from the selected times by region. For example, the image is output representing a planar region. The displacement region of interest is an entire B-mode scan region or part of a B-mode scan region.

For the locations in the region for which displacements are measured (e.g., same or different sampling density than the B-mode scan), displacements from the selected times are used to generate the image. In the line-by-line example, different lines of the image or different linear portions (e.g., where scan conversion changes the format) correspond to the same or different time relative to respective ARFIs. Each ARFI repetition contributes the displacements and time selection for different portions of the region of interest. Alternatively, the displacements for the single time are used for generating the image.

The pixels or display values of the image are modulated by the displacements of the selected time or times. The displacements map to the color, gray scale, brightness, hue, or other characteristic of a display pixel. For example, a range of colors are mapped where red indicates greater displacement and blue indicates lesser displacement.

The ARFI image represents the displacements at a particular time or collection of times by region. Pixel-by-pixel selection, such as the maximum, is avoided, instead using regional selection where the region is more than one pixel. While one or more regions may indicate the maximum, the maximum is not specifically sought. Accumulation is avoided. Instead, displacements for instants in time without accumulating maximum displacements are used. The displacements associated with the desired cost, such as contrast and SNR, are used for the ARFI image.

In the example of FIGS. 1A-D, the maximum displacement image of FIG. 1A is not displayed. Instead, one of the other images from a specific time is displayed. Using the example contrast multiplied by SNR selection, the displacements at 0.63 are selected, resulting in display of the ARFI image shown in FIG. 1D. The maximum displacement image may be displaced adjacent to or sequentially with the time instant ARFI image.

The ARFI image may be combined with other image information. For example, the ARFI image is displayed as a color overlay of a B-mode image. The ARFI image may be overlaid or combined with any one or more other modes of imaging. Where the ARFI image and other images represent the same spatial locations, one source (e.g., ARFI or B-mode) is used for display or the information from the different sources are combined (e.g., averaged or mapped to different characteristics of the pixel).

In one embodiment, the ARFI image is generated as a blend of maximum displacement and the displacements from the selected time. Blending may result in the advantages of both being included in the resulting ARFI image. Any blend may be used, such as mapping to different characteristics (e.g., one to gray scale and the other to color) or averaging. In one example, the image is a combination of the maximum displacements and the displacements of a selected time or times. The combination is a weighted blend, such as Final Image=alpha*Max Displacement Image+(1−alpha)*Optimal Time Instance Displacement Image. Alpha is predetermined, user selectable, application specific, or another value to relatively weight the contribution from the different displacements. Rather than blending the pixel or display values for the different sources, the displacement values may be blended prior to mapping to the display values.

The image may be generated for other elasticity characteristics. The displacements for the selected time are used to determine shear velocity, modulus, or other information representing tissue reaction to a shear, longitudinal, or other wave. Any shear or other wave imaging may be used.

Figure 4:
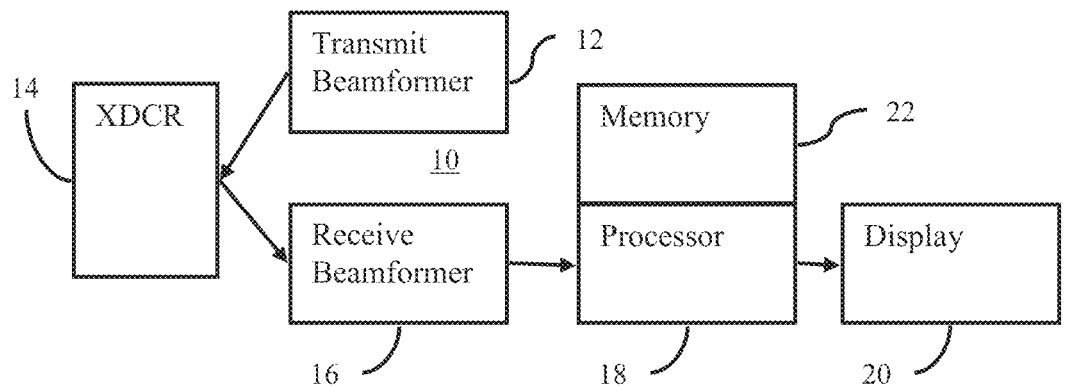
FIG. 4 is a block diagram of one embodiment of a system for ARFI imaging with temporal selection.

FIG. 4 shows one embodiment of a system 10 for acoustic radiation force imaging (ARFI). The system 10 implements the method of FIG. 2 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system, such as to configure the cost function and/or blending for a given situation.

The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, digital-to-analog converter, amplifier, delay, phase rotator, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waveforms, one or more beams are formed. Multi-beam transmission may be used. A sequence of transmit beams are generated to scan a one, two or three-dimensional region. Sector, Vector®, linear, or other scan formats may be used. The same region is scanned multiple times. For flow or Doppler imaging and for shear or other wave imaging, a sequence of scans is used. In Doppler and ARFI imaging, the sequence may include multiple beams along a same scan line before scanning an adjacent scan line. For ARFI or elasticity imaging, scan or frame interleaving may be used (i.e., scan the entire region before scanning again). In alternative embodiments, the transmit beamformer 12 generates a plane wave or diverging wave for more rapid scanning.

The same transmit beamformer 12 generates impulse excitations or electrical waveforms for generating acoustic energy to cause displacement. The transmit beamformer 12 causes the transducer 14 to generate high intensity focused ultrasound waveforms. In alternative embodiments, a different transmit beamformer is provided for generating the impulse excitation.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event provides a pulse of ultrasound energy for displacing the tissue. The pulse is an impulse excitation. Impulse excitation includes waveforms with many cycles (e.g., 500 cycles) but that occur in a relatively short time to cause tissue displacement over a longer time.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The transducer 14, in response to the transmit beamformer 12, transmits a sequence of acoustic impulse excitations into the patient. The excitations are to different regions, such as different lines or groups of lines. The transducer 12, in response to the transmit beamformer 12 and the receive beamformer 16, also transmits and receives acoustic energy for monitoring the response of the tissue to the excitations. The tissue is scanned multiple times for a group of locations after each impulse excitation to measure displacement at different times relative to the respective impulse excitation.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or scanning transmission. Dynamic focusing may be provided. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

In coordination with the transmit beamformer 12, the receive beamformer 16 generates data representing the region (e.g., a scan line or group of scan lines) at different times. After the acoustic impulse excitation, the receive beamformer 16 generates beams representing different lines or locations at different times. By scanning the region of interest with ultrasound, data (e.g., beamformed samples) are generated. The scanning may be performed for different sub-regions using different impulse excitations, so the receive beamformer 16 generates data representing the different sub-regions (e.g., different scan lines) at multiple, different times relative to the respective impulse excitations.

The receive beamformer 16 outputs beam summed data representing spatial locations. Data for a single location, locations along a line, locations for an area, or locations for a volume are output. The data may be for different purposes. For example, different scans are performed for B-mode or tissue data than for displacement. Alternatively, the B-mode data is also used to determine displacement.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof, or other now known or later developed device for detecting and processing information for display from beamformed ultrasound samples. In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement and selecting a time or times and corresponding displacements relative to the impulse excitations. The processor 18 may control other components, such as the transmit and receive beamformers 12, 16. For example, the separate processor is configured by hardware and/or software to cause the beamformers 12, 16 to perform acts 30 and 32 and to perform any combination of one or more of the acts 34-42 shown in FIG. 1.

The processor 18 is configured to estimate tissue displacement induced by the acoustic impulse excitation. Using correlation, tracking, motion detection, or other displacement measuring, the amount of shift in position of the tissue is estimated. The estimation is performed multiple times through a period, such as from prior to the tissue moving due to the impulse to after the tissue has mostly or completely returned to a relaxed state (e.g., recovered from the stress caused by the impulse excitation). Shorter or longer periods of measuring may be used.

The processor 18 is configured to estimate the tissue displacements in a line-by-line, group of line-by-group of line or other region-by-region manner. The displacements are estimated along one or more lines in response to a given impulse excitation. The displacements for another line or other lines are estimated in response to a different impulse excitation. The same or different temporal sampling is used in each sequence. Other regions than lines may be used, such as area by area or volume by volume.

The processor 18 is configured to select a time from the different times for each region, such as each line or group of lines. An instant for tissue displacements along the line or group is selected. The same selection is performed for other lines or groups of lines. The timing is relative to the respective impulse excitation. Since the selection is performed for each of the regions (e.g., lines), the time selected for one line is the same or different than times selected for other lines relative to the respective impulse excitations.

Any criteria may be used for the selection. For example, contrast, signal-to-noise ratio, another parameter, or combinations thereof are used to select the time. As another example, the time-to-maximum is selected. The characteristic of the displacements is examined to determine the displacements with the desired characteristics. Information from other sources than the displacements may be used. By comparing the characteristics at different times, the time corresponding to the displacements with the best characteristics for the situation is determined. The corresponding displacements may be used for further processing.

The processor 18 is configured to generate an image. The selected displacements or information derived therefrom are mapped to display values. Scan conversion is performed before or after calculating displacements, selecting displacements, or generating the image.

The image is responsive to different sequences of scanning. Different parts of the ARFI image may correspond to selection of displacements associated with a relative time different from each other. The image is assembled from the corresponding displacements. The processor 18 outputs the display values as an image to the display 20.

The display 20 is a CRT, LCD, projector, plasma, or other display for displaying two-dimensional images or three-dimensional representations. The display 20 is configured by the processor 18 or other device by input of the signals to be displayed as the ARFI image. The display 20 displays an image representing displacement or elasticity for different locations in a region of interest or an entire image. The displacements with the desired characteristics are used in the ARFI image to assist in diagnosis.

The image represents the displacements for one region (e.g., line) from one time and the other region (e.g., line) from another time relative to the respective impulse excitation. For example, one impulse excitation is transmitted at time 0.00 for a first line. The tissue displacement along the first line or in a region around the first line (e.g., along multiple lines) is monitored from 0.01 ms to 0.75 ms. The process (e.g., transmit ARFI and monitor) is repeated for a different line or group of lines from 1.0 ms to 1.75 ms. With monitoring at a sampling rate of 0.01 ms, 74 scans occur for each sequence. The scans on the different lines at 0.01 ms and 1.01 ms have the same 0.01 ms time relative to the respective impulse excitation. As a result, the ARFI image may have displacements for one line from the 0.43 ms and for the other line from 1.43 ms with the same relative timing or for the other line from 1.55 ms with different relative timing.

The processor 18 operates pursuant to instructions stored in the memory 22 or another memory for classification pre-processing in medical ultrasound shear wave imaging. The processor 18 is programmed for acoustic radiation force imaging (ARFI). The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for acoustic radiation force impulse (ARFI) imaging, the method comprising:
   transmitting an acoustic radiation force impulse into a patient;
   measuring, with an ultrasound system, displacements of tissue over different times at each of a plurality of locations within a patient, the displacements being in response to the acoustic radiation force impulse;
   determining contrasts for the displacements at each of the times, each contrast being a difference in at least some of the displacements for one of the times;
   determining signal-to-noise ratios for the displacements at each of the times;
   selecting a first one of the times based on the contrasts and the signal-to-noise ratios; and
   generating an ARFI image with the displacements of the selected first time.

2. The method of claim 1 further comprising:
   the impulse excitation comprising the acoustic excitation;
   wherein measuring the displacements over the different times comprises repetitively scanning with ultrasound.

3. The method of claim 1 wherein measuring the displacement comprises transmitting ultrasound to the tissue and receiving reflections from the transmitting, the transmitting the ultrasound and receiving being repeated for the different times, and detecting the displacements from the reflections of the multiple receiving from multiple locations.

4. The method of claim 1 wherein measuring comprises measuring the displacements along a scan line.

5. The method of claim 4 further comprising repeating the measuring, determining contrasts, determining signal-to-noise ratios and selecting for additional scan lines, where generating the ARFI image comprises generating from the displacements of the scan line and the additional scan lines of the respective selected times including the first time.

6. The method of claim 1 wherein determining contrasts for the displacements at each of the times comprises subtracting a minimum of the displacements for each time from a respective maximum of the displacements for the respective time.

7. The method of claim 1 wherein determining the signal-to-noise ratios comprises:
   filtering the displacements over the locations for each time;
   subtracting the filtered displacements from the displacements for each time;
   dividing the displacements by a result of the subtracting.

8. The method of claim 1 wherein selecting comprises selecting the first time as the time with a maximum of the contrast multiplied by the signal-to-noise ratio.

9. The method of claim 1 wherein selecting comprises selecting with a cost function including the contrasts and signal-to-noise ratios as input variables.

10. The method of claim 1 wherein generating comprises generating the ARFI image with the displacements being other than maximum displacements over the different times.

11. The method of claim 1 wherein generating comprises generating the ARFI image with the displacements of the first time.

12. The method of claim 1 wherein generating comprises generating the ARFI image as a blend of a maximum displacement and the displacements of the first time.

13. A method for acoustic radiation force impulse (ARFI) imaging, the method comprising:
   transmitting an acoustic radiation force impulse into a patient thereby displacing tissue at a plurality of locations within the patient;
   measuring, with an ultrasound system, displacements of the displaced tissue at the plurality of locations within the patient at a plurality of times in response to the acoustic radiation force impulse;
   determining, for each time of the plurality of times, contrast parameter for the displacements by subtracting a minimum of the displacements from a respective maximum of the displacements for the respective time;
   determining, for each time of the plurality of times, signal-to-noise ratio for the displacements for the respective time;
   selecting from the plurality of times, a time that maximizes a product of the contrast parameter multiplied by the signal-to-noise ratio; and
   generating an ARFI image with the measured displacements of the selected time.

14. The method of claim 13 wherein measuring comprises measuring the displacements along a scan line.

15. The method of claim 14 further comprising repeating the measuring, determining contrast parameter, determining signal-to-noise ratio and selecting for additional scan lines, where generating the ARFI image comprises generating from the displacements of the scan line and the additional scan lines of the respective selected times including the first time.

16. The method of claim 13 wherein determining the signal-to-noise ratio comprises:
   filtering the displacements over the locations for each time;
   subtracting the filtered displacements from the displacements for each time;
   dividing the displacements by a result of the subtracting.

17. The method of claim 13 wherein selecting comprises selecting with a cost function including the contrasts and signal-to-noise ratios as input variables.

18. The method of claim 13 wherein generating comprises generating the ARFI image with the displacements being other than maximum displacements over the different times.

19. The method of claim 13 wherein generating comprises generating the ARFI image as a blend of a maximum displacement and the displacements of the first time.

* * * * *